(12) United States Patent
Howard et al.

(10) Patent No.: US 9,090,550 B2
(45) Date of Patent: *Jul. 28, 2015

(54) MICROWAVE ASSISTED SYNTHESIS OF DEHYDRATED SUGAR DERIVATIVES HYDROXYMETHYLFURFURAL, LEVULINIC ACID, ANHYDROSUGAR ALCOHOLS, AND ETHERS THEREOF

(75) Inventors: Stephen J. Howard, Sherman, IL (US); Alexandra J. Sanborn, Lincoln, IL (US)

(73) Assignee: Archer Daniels Midland Company, Decatur, IL (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/811,759

(22) PCT Filed: Jul. 18, 2011

(86) PCT No.: PCT/US2011/044324
§ 371 (c)(1),
(2), (4) Date: Jan. 23, 2013

(87) PCT Pub. No.: WO2012/015616
PCT Pub. Date: Feb. 2, 2012

(65) Prior Publication Data
US 2013/0123520 A1    May 16, 2013

Related U.S. Application Data

(60) Provisional application No. 61/369,350, filed on Jul. 30, 2010.

(51) Int. Cl.
| | |
|---|---|
| *C07C 59/185* | (2006.01) |
| *C07D 307/48* | (2006.01) |
| *C07D 307/93* | (2006.01) |
| *C07D 307/46* | (2006.01) |
| *C07C 67/00* | (2006.01) |
| *C07D 307/50* | (2006.01) |
| *C07D 493/04* | (2006.01) |

(52) U.S. Cl.
CPC ............... *C07C 59/185* (2013.01); *C07C 67/00* (2013.01); *C07D 307/46* (2013.01); *C07D 307/48* (2013.01); *C07D 307/50* (2013.01); *C07D 307/93* (2013.01); *C07D 493/04* (2013.01)

(58) Field of Classification Search
CPC .... C07C 67/00; C07C 59/185; C07C 69/716; C07D 307/46; C07D 307/48; C07D 307/50; C07D 307/93; C07D 493/04
USPC ........................... 549/464, 488, 489; 560/174
See application file for complete search history.

(56) References Cited

U.S. PATENT DOCUMENTS

| | | | |
|---|---|---|---|
| 5,558,899 A | 9/1996 | Kuzee et al. | |
| 7,420,067 B2 * | 9/2008 | Sanborn | 549/465 |
| 8,445,705 B2 * | 5/2013 | Howard et al. | 549/464 |
| 2007/0213544 A1 | 9/2007 | Sanborn et al. | |
| 2009/0156841 A1 * | 6/2009 | Sanborn et al. | 549/488 |
| 2009/0281338 A1 * | 11/2009 | Sanborn | 549/488 |

OTHER PUBLICATIONS

Hansen et al, Carbohydrate Research, 2009, 344, 2568-2572.*
Qi et al, Green Chemistry, 2008, 10, 799-805.*
Shaikh et al, Chemical Reviews, 1996, 96, 951-976.*

* cited by examiner

*Primary Examiner* — Ganapathy Krishnan
(74) *Attorney, Agent, or Firm* — Mark W. Roberts; Alexandra Sanborn

(57) ABSTRACT

Methods for the production of dehydrated sugars and derivatives of dehydrated sugars using microwave (MW) irradiation and methods of purifying the same are described. The dehydrated sugars derivatives include 5-hydroxymethyl-2-furfural (HMF) and anhydrosugar alcohols such as sorbitans and isosorbide. The derivatives include HMF ethers, levulinic acid esters, and ether derivatives of the anhydrosugar alcohols. The described methods require lower reaction temperatures and shorter reaction times than similar non microwave mediated reactions known in the art. Typical reaction conditions are 120-210° C., and typical reaction times are 30 minutes or less.

6 Claims, 2 Drawing Sheets

MICROWAVE ASSISTED SYNTHESIS OF DEHYDRATED SUGAR DERIVATIVES HYDROXYMETHYLFURFURAL, LEVULINIC ACID, ANHYDROSUGAR ALCOHOLS, AND ETHERS THEREOF

CROSS REFERENCE TO REPLATED APPLICATIONS

This application claims priority to PCT application No. PCT/US2011/044324 filed Jul. 18, 2011, which claims priority to U.S. provisional application No. 61/369,350 filed Jul. 30, 2010.

TECHNICAL FIELD

The present disclosure relates to improved methods of producing the dehydrated sugar derivatives such as 2,5-(hydroxymethyl)furfural, levulinate esters, anhydrosugar alcohols as well as ether and ester derivatives thereof using microwave radiation to catalyze the reactions.

BACKGROUND

The principle sugars from plant materials, glucose and fructose, have been shown to be useful renewable starting materials for the production of a variety of organic compounds that may substitute for petroleum based compounds. For example, the furan compound, 2,5-(hydroxymethyl)furaldehyde, also known as 2,5-(hydroxymethyl)furfural (HMF) a five membered heterocycle obtained by dehydration of a hexose, most efficiently from fructose.

HMF has strong potential in industrial and commercial applications especially for polymer applications due to its multi-functionality which allows for use as a monomer in polymerization reactions.

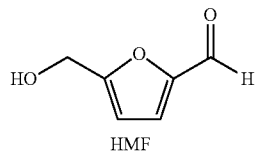

HMF

Generation of HMF by dehydration of fructose produces three equivalents of water as by products, and the formation of 3 double bonds (two alkenes and one aldehyde). In order to compete as substitutes or replacements in the chemicals market, HMF must be produced at relatively low cost. The production of HMF has been studied for years, but an efficient and cost-effective method of producing HMF has yet to be found. Extended reaction times, high temperatures and pressures cause complications to arise from the rehydration of HMF after the dehydration occurs, which often yields the byproducts of levulinic acid and formic acid. Another competing side reaction is the polymerization of HMF and/or fructose to form humin.

A low yield of HMF is typically obtained when the synthesis is performed in aqueous conditions because of the low selectivity of the dehydration reaction. Low selectivity simultaneously leads to increased polymerization reactions and humin formation, which also interfere with the synthesis of HMF. Where attempts have been made to solve problems associated with aqueous systems, the HMF reaction product is generally sequestered by organic solvent extraction or adsorption onto a resin as soon as it is formed. These systems fail to directly address the issue of low selectivity for HMF. In addition, these systems generally suffer from high dilution or partially irreversible adsorption of HMF and increase cost due to handling and use of the organic solvents or resins. Thus, a selective aqueous reaction system wherein HMF is the predominant product formed at would be desirable.

Levulinic acid is made by dehydration of hexose, which generates HMF as an intermediate, followed by deformylation resulting in the loss of formic acid. Levulinic acid and levulinate esters have been used as important intermediates in pharmaceutical and fine chemical processes.

Levulinic Acid

Anhydrosugar alcohols, such as sorbitan and isosorbide derived from glucose, are mono cyclic and bi-cyclic ring compounds that are made by the dehydration of 1 or 4 water molecules, respectfully, from a hexitol, which is typically made by hydrogenation of a hexose.

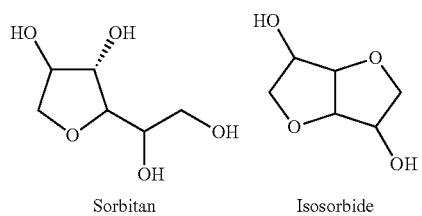 [SMILES: OCC(O)C1OCC(O)[C@@H]1O ; OC1COC2C(O)COC12]

Sorbitan         Isosorbide

Of all the known isohexides, isosorbide is considered to be one of high importance because of its use in the formation of pharmaceutical compounds, in food production, cosmetic production, plastic and polymer production, and in other potential industrial uses such as in the production of polyurethane, polycarbonate, polyesters, and polyamides (Stoss and Hemmer, 1991).

Several processes for the production of anhydrosugar alcohols (including isohexides such as isosorbide) have been reported. For example, PCT application number PCT/US99/00537 (WO 00/14081), discloses collecting methods and a continuous production method with recycling of organic solvent. Most methods involve the use of concentrated acids and organic solvents. Goodwin et al., Carbohydrate Res. 79:133-141 (1980) have disclosed a method involving the use of acidic-cation-exchange resin in place of concentrated, corrosive acids, but with low yield of isosorbide product. An alternative is the supersaturation-based method, as disclosed in U.S. Pat. No. 4,564,692 (Feldmann, et al., Jan. 14, 1986). However, a need continues for a process for production of very pure dianhydrosugaralcohols, at reasonable yields.

These dehydrated ring derivatives of hexoses, may further be used for making several other compounds, for example, by making ether derivatives of the free alcohol groups as illustrated below:

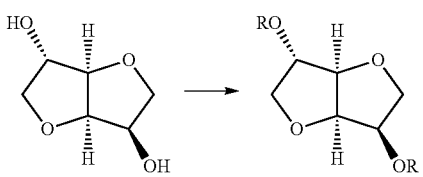

Where R can be alkyl, allyl, or aryl

For example, the anhydrosugar alcohol, isosorbide, can be used as a starting material in the formation of isosorbide dimethyl ether and isosorbide dinitrate or as an intermediate in various organic synthesis reactions. Isosorbide dimethyl ether is useful as an industrial solvent, a pharmaceutical additive, and in personal care products, while isosorbide dinitrate is useful as a medication to relieve the pain of angina attacks or reduce the number of such attacks by improving blood flow to the heart.

Accordingly, there is a need in the art to find methods of making a variety dehydrated sugar compounds and derivatives thereof that is cost effective and efficient.

BRIEF SUMMARY

Methods of producing a variety of dehydrated sugar derivatives are provided. Commonly, for any of the dehydrated sugar derivatives the methods include forming a reaction mixture comprising a solvent and a reactant selected from the group consisting of a hexose, a sugar alcohol, and an anhydrosugar alcohol; and contacting the mixture with microwave radiation bringing it to temperature of between 130° C. and 220° C. for a time sufficient to convert at least 40% of the reactant into at least one desired dehydrated sugar derivative product.

In one aspect, the reactant is a hexose and the desired dehydrated sugar derivative is HMF. In a particular embodiment of this aspect, the hexose is fructose. In a typical embodiment, the reaction mixture further includes an acid catalyst.

In another aspect, the reactant is a sugar alcohol and the desired dehydrated sugar derivative is an anhydrosugar alcohol. In a particular embodiment of this aspect, the sugar alcohol is sorbitol and the reaction product is sorbitan or isosorbide. In a typical embodiment, the reaction mixture further includes an acid catalyst. In typical practices the temperature range is 130° C.-190° C.

In another aspect the reactant is a hexose, the reaction mix contains an R-alcohol and the reaction product is an ether of HMF. In a similar aspect, the product is a levulinate ester. Glucose is preferred for making the levulinate esters. In a typical embodiment, the reaction mixture further includes an acid catalyst.

In those aspects where an acidic catalyst may be used, the catalyst is selected from the group consisting of a solid acid substrate and a homogeneous acid.

In embodiments where an R-alcohol R can be an alkyl, allyl, cycloalkyl, or aryl group, and the desired dehydrated sugar derivative is selected from the group consisting of an R-ether or R-ester of the desired dehydrated sugar derivative. In a typical practice, the e R-alcohol is the solvent of the reaction mixture. In those embodiments where the reactant is a hexose the desired dehydrated sugar derivative is selected from the group consisting of R-oxy HMF, and R acyl-levulinate.

In those aspects where an anhydrosugar alcohol is desired, in exemplary embodiments the reactant is sorbitol, the reaction mixture contains an acid catalyst, the temperature is between 130° C. and 190° C. and the desired dehydrated sugar derivative comprises a combination of sorbitan and isosorbide. Typically, the desired dehydrated sugar derivative is predominantly sorbitan.

In certain embodiments where reactant is the anhydrosugar alcohol and it is desired to make an ether derivative of the anhydrosugar alcohol, the reaction mixture further contains R-carbonate where R is an alkyl, allyl, cycloalkyl, or aryl group, the solvent is not water, the reaction mixture contains an organic base catalyst, and the desired dehydrated sugar derivative is an R-anhydrosugar alcohol ether. In an exemplary embodiment, isosorbide is the reactant and the dehydrated sugar derivative is mono- or di-R oxy isosorbide.

In most practices greater than 40%, or greater than 50% of the reactant is converted into the desired dehydrated sugar derivatives. Many embodiments further include at least partially purifying the desired dehydrated derivative from the reaction mixture. In a typical practice, the partial purification includes adding an immiscible organic solvent to the mixture thereby partitioning the dehydrated sugar derivative into immiscible organic solvent solution, collecting the partitioned immiscible organic solvent, and evaporating the collected solvent to produce an extract enriched in the desired dehydrated sugar derivative. Suitable immiscible organic solvent can selected from ethyl acetate, methyl t-butyl ether, diethyl ether, toluene, methyl ethyl ketone, ethyl lactate, methyl isobutyl ketone, octanol, pentanol, butyl acetate, chloroform, and any combinations thereof. In a particularly desirable embodiment, the starting reactant is fructose, the dehydrated sugar derivative is HMF, the reaction mixture contains and acid catalyst, and the reaction solvent is selected from a group consisting of: dimethylacetamide, dimethylformamide, N-methyl pyrrolidinone, and HMF is purified by partitioning it from the reaction solvent into the immiscible organic solvent.

DETAILED DESCRIPTION

Figure 2:
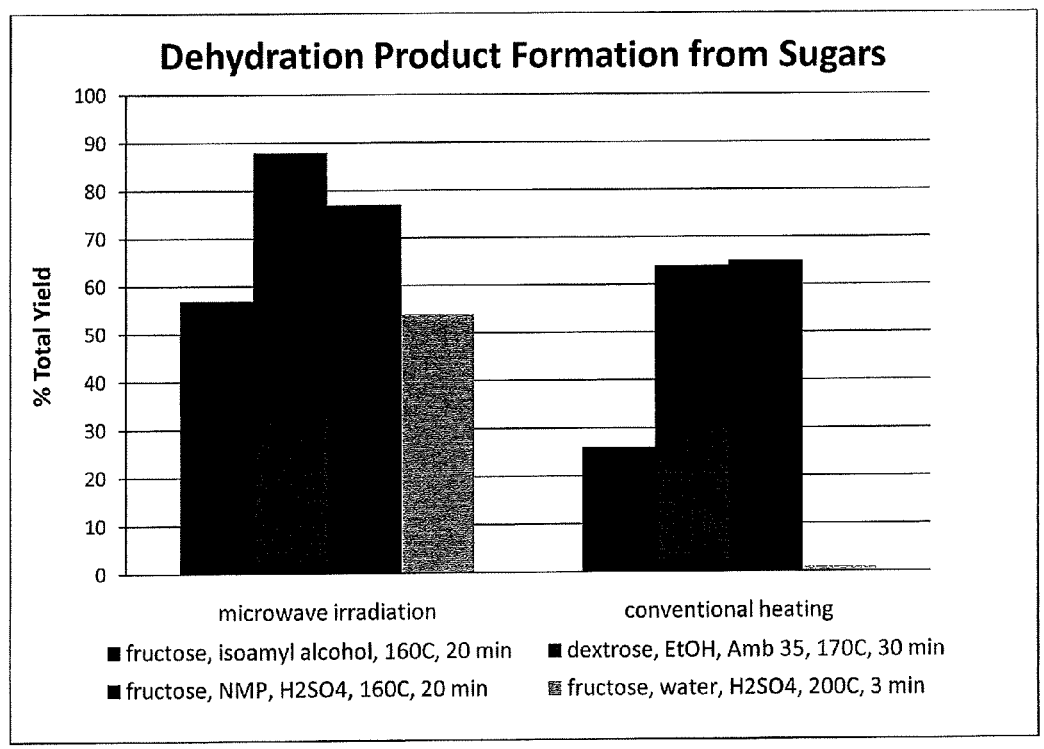
FIG. 2 is a chart showing the effect of microwave radiation on the dehydration of sugars in comparison to non-microwave methods.

Disclosed herein are methods of improved synthesis of dehydrated sugar derivatives and ethers and esters thereof. The disclosure is based on the surprising discovery that microwave radiation increases yield and selectivity, while lowering the temperature and time needed to perform dehydration and derivative reactions with sugars. Typically, when used in the presence of a conventional catalyst for such reactions, temperatures in the range of 130 to 180° C. can be used for periods of about 30 minutes or less to obtain comparable yields and selectivity obtained at temperatures of 200-250° C. using the same reagents and catalyst system without the microwave radiation. Because the temperature is so much lower using the microwave enhance radiations, the catalytic function of the microwave energy must be more than just providing heat to the reaction mixture. FIG. 2 shows a direct comparison of total product yields from sugar dehydration using microwave radiation vs non-microwave methods. By microwave radiation, total product yields are enhanced.

While not being bound by theory, it is believed that microwave energy preferentially activates the carbon-oxygen-hydrogen bonds involved in dehydration and hydrolytic condensation, thereby facilitate faster dehydration and bond formation at lower energy levels than required by conventional heating.

HMF and HMF derivatives, such as HMF ethers and esters, and levulinic acid and derivatives, such as levulinate esters are provided. Such methods provide the advantages of higher starting concentrations, enhanced reaction rates, high selectivity for the reaction product of choice, ease of manipulation, and precise control over reaction conditions. In certain embodiments, processes are disclosed involving microwave exposure of reactants either in the presence of an aqueous or organic solvent and may be performed with or without a catalyst.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims, may be read as if prefaced by the word "about" even though the term "about" may not expressly appear with the value, amount, or range. Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

It should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is identified herein is incorporated by reference herein in its entirety, but is incorporated herein only to the extent that the incorporated material does not conflict with existing definitions, statements, or other disclosure material set forth in this disclosure. As such, and to the extent necessary, the disclosure as explicitly set forth herein supersedes any conflicting material said to be incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As would be understood in the art, the term "microwave irradiation" refers to electromagnetic waves comprising frequencies of 300 Megahertz (MHz) to 300 Gigahertz (GHz). In certain embodiments, the microwave irradiation range comprises an alternating current signal with a frequency in a range of 300 MHz to 300 GHz. In other embodiments, the microwave irradiation comprises an alternating current signal with a frequency in the range of 300 MHz to 30 GHz. In still other embodiments, the microwave irradiation range comprises an alternating current signal with a frequency in the range of 300 MHz to 3 GHz.

The starting materials for the reactions described herein are sources of sugars and dehydrated sugar derivatives. Examples of sugar sources that may be converted to HMF or HMF ethers and levulinic acid esters as well as combinations thereof, include, but are not limited to any source of a sugar, including for example, any hexose, polysaccharides comprising at least one hexose, pentose, corn syrup, a dissolved crystalline fructose, high-fructose corn syrup which is typically a 45 to 75% wt/wt mixture of fructose with glucose made by isomerization of ordinary corn syrup, high-fructose corn syrup refinery intermediates and by-products such as mother liquor, ordinary corn syrup, which is the glucose syrup obtained from direct hydrolysis of corn starch, process streams from making fructose or glucose, sucrose, sugar cane molasses, and any combinations thereof. The source of the sugar is not important because all sugars will undergo the dehydrations and hydrolytic synthesis reactions to produce the derivatives described herein, however, the reaction products and selectivity of the reactions will of course vary with the particular source of sugar. Where the desired reaction product is HMF or a derivative of HMF, it is preferred to use a source that contains larger amounts of fructose. Where the desired reaction product is a levulinic acid ester, the desired starting material should contain larger amounts of glucose.

The reactions provided herein are capable of producing relatively high yields of products As used throughout in the present disclosure herein, "reaction yield" is calculated using the equation (moles of HMF produced/moles of fructose consumed)×100. Product purity is reported on a weight percent basis. For example, in certain embodiments, greater than 25% of the sugar can be converted to HMF or HMF ethers and esters and levulinic acid and levulinate esters, as well as combinations thereof. In other embodiments, greater than 50% of the sugar, such as hexose, can be converted to HMF or HMF ethers and esters, as well as combinations thereof. In yet other embodiments, greater than 70% or more of the sugar, such as hexose, can be converted to HMF or HMF ethers and esters, as well as combinations thereof.

The present disclosure provides various features and aspects of the exemplary embodiments provided herein. It is understood, however, that the disclosure embraces numerous alternative embodiments, which may be accomplished by combining any of the different features, aspects, and embodiments described herein in any combination that one of ordinary skill in the art may find useful.

To synthesize HMF in a microwave reactor, a hexose source—most preferably one containing fructose—is combined with a solvent, and optionally with a catalyst to form a mixture that irradiated with microwaves for a sufficient time to convert at least a portion of the sugar into HMF.

In certain embodiments, the reaction mixture includes an acid catalyst, Suitable examples of acid catalysts include homogenous acids such as dissolved inorganic acids, soluble organic acids, soluble Brnsted-Lowry acids, and heterogeneous solid acid catalysts, acidic ion-exchange resins, acid zeolites, Lewis acids, acidic clays, molecular sieves, and any combinations thereof. In typical embodiments the homogeneous acid may have a range of 0.1% to 10% by weight starting sugar. In typical embodiments, the homogeneous acid may have a range of 1% to 10% by weight. In other embodiments, the homogeneous acid may have a range of 0.1% to 5% by weight. The heterogeneous solid acid catalysts often comprise a solid material which has been functionalizing to impart acid groups that are catalytically active. Solid acid catalysts may have a broad range of composition, porosity, density, type of acid groups, and distribution of acid groups. Solid acid catalysts may be recovered and reused, optionally with a treatment to regenerate any activity that may have been lost in use. Some solid acid catalysts that may be used include, but are not limited to, Amberlyst 35, Amberlyst 36, Amberlyst 70, Amberlyst 15, Amberlyst 131 (Rohm and Haas, Woodridge, Ill.), Lewatit 52328, Lewatit K2431, Lewatit S2568, Lewatit K2629 (Sybron Corp, Birmingham, N.J.), Dianion SK 104, Dianion PK228, Dianion RCPI60, RCP21H, Relite RAD/F (Mitsubishi Chemical, White Plains, N.Y.), Dowex 50WX4 (Dow Chemical) and any combination thereof. In certain embodiments of the present disclosure, the solid acid catalyst may have a range of 1% to 50% by weight. In some embodiments, the solid acid catalyst may have a range of 1% to 25% by weight. In other embodiments, the solid acid catalyst may have a range of 1% to 10% by weight.

In exemplary embodiments, either a heterogeneous solid acid catalyst like Amberlyst 35 resin, or a homogeneous acid catalyst exemplified by $H_2SO_4$ was used. In preferred reactions, the reaction contains fructose, is conducted in an organic solvent, the microwave radiation is used to raise and hold the temperature to between 120 and 170° C., typically from between 130 and 160° C. and reaction time is sufficient to convert at least 40% of the fructose to HMF in 15 minutes. In higher yield reactions, the temperature is between 140 and 160° C., the time is less than 30 minutes—more like 20 minutes, and at least 65% of the fructose is converted to HMF. Typically these reaction conditions were conducted using a ramp up to temperature time of 1.5 to 3 minutes.

Suitable organic solvents for the reaction mixture are polar organic aprotic solvents. Examples of possible solvents include, but are not limited to, 1-methyl-2-pyrrolidinone, dimethylacetamide, dimethylformamide, dimethyl sulfoxide, methyl ethyl ketone, methyl isobutyl ketone, acetonitrile, propionitrile, and any combinations thereof.

Suitable heterogeneous acids catalysts that may be used include, but are not limited to, Amberlyst 35, Amberlyst 36, Amberlyst 70, Amberlyst 15, Amberlyst 131 (Rohm and Haas, Woodridge, Ill.), Lewatit 52328, Lewatit K2431, Lewatit 52568, Lewatit K2629 (Sybron Corp, Birmingham, N.J.), Dianion SK 104, Dianion PK228, Dianion RCPI60, RCP21H, Relite RAD/F (Mitsubishi Chemical, White Plains, N.Y.), Dowex 50WX4 (Dow Chemical) and any combination thereof. In certain embodiments of the present disclosure, the solid acid catalyst may have a range of 1% to 50% by weight. In some embodiments, the solid acid catalyst may have a range of 1% to 25% by weight. In typical embodiments, the solid acid catalyst is used at a range of 1% to 10% by weight of the starting sugar.

Suitable homogeneous acids that may be used include inorganic acids such as such as $H_2SO_4$, $H_3PO_4$, HCl, as well as strong organic acids such as oxalic acid, levulinic acid, and p-toluene sulfonic acid.

Other catalysts not exemplified may also be used. These include, but are not limited to boron trifluoride etherate, and metals, such as Zn, Al, Cr, Ti, Th, Zr, and V.

Although use of an organic solvent and a catalyst is preferred, neither are necessary to obtain suitable yields. The reaction may, for example, be conducted in an aqueous solvent with or without added catalyst. Under aqueous conditions without catalyst, the reaction temperature should be brought to about 200-210° C. using the microwave radiation, however, the time should be shortened to less than 5 minutes to avoid rehydration and production of levulinic acid and other non selective by-products. Yields of greater than 50% HMF from fructose were obtained in an aqueous solvent in the absence of acid catalyst at reaction temperatures of 200-210° C. for 3 to 3.5 minutes after a 3 to 3.5 minute ramp up to temperature. When sulfuric acid is used in an aqueous solvent, the reaction temperature and can be reduced to 130-170° C. and the time increased to 10-20 minutes.

Figure 1:
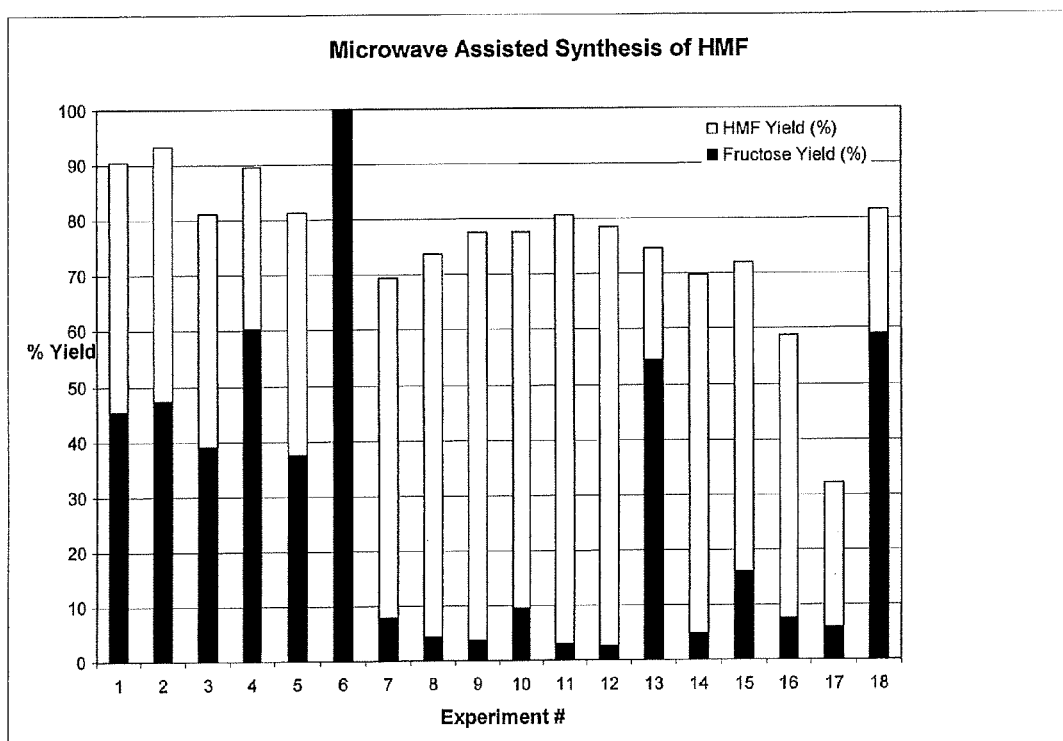
FIG. 1 is a chart showing conversion of HMF from fructose using microwave radiation according to a series of experiments performed in accordance with one aspect of the present invention.

Table 1 and FIGS. 1 and 2 illustrate data from several experiments showing the production and yield of HMF from fructose with microwave radiation under various conditions.

TABLE 1

Conversion of Fructose to HMF at lower temperatures in shorter time periods using microwave irradiation graphically illustrated in FIG. 1.

| Experiment # | Acid (%) | Solvent | Temp (C.) | Time (min) | Water (%) | Fructose Yield (%) | HMF Yield (%) | Unknown Yield (%) | Conversion (%) |
|---|---|---|---|---|---|---|---|---|---|
| 1 | 50% Amberlyst 35 | DMF | 130 | 5 | 10.22 | 45.44 | 44.96 | 0.00 | 82.40 |
| 2 | 50% Amberlyst 35 | DMF | 130 | 10 | 9.4 | 47.36 | 45.92 | 0.00 | 87.23 |
| 3 | 50% Amberlyst 35 | DMF | 130 | 15 | 8.35 | 39.05 | 42.06 | 10.55 | 69.00 |
| 4 | 50% Amberlyst 35 | DMAc | 130 | 10 | 10.96 | 60.37 | 29.24 | 0.00 | 73.77 |
| 5 | 50% Amberlyst 35 | DMAc | 130 | 15 | 10.96 | 37.59 | 43.84 | 7.61 | 70.24 |
| 6 | 50% Amberlyst 35 | Water | 130 | 15 | 76.38 | 100.00 | 0.00 | 0.00 | 0.00 |
| 7 | 0.9% H2SO4 | nmp | 160 | 10 | 6.05 | 7.87 | 61.58 | 24.50 | 66.84 |
| 8 | 0.9% H2SO4 | nmp | 160 | 20 | 7.09 | 4.27 | 69.47 | 19.16 | 72.57 |
| 9 | 0.9% H2SO4 | nmp | 160 | 30 | 7.48 | 3.75 | 73.97 | 14.80 | 76.85 |
| 10 | 1.8% H2SO4 | nmp | 160 | 10 | 6.83 | 9.44 | 68.17 | 15.56 | 75.27 |
| 11 | 1.8% H2SO4 | nmp | 160 | 20 | 6.86 | 3.03 | 77.68 | 12.43 | 80.10 |
| 12 | 1.8% H2SO4 | nmp | 160 | 30 | 7.46 | 2.53 | 76.08 | 13.94 | 78.05 |
| 13 | 1.8% H2SO4 | water | 140 | 10 | 72.98 | 54.52 | 20.05 | 25.43 | 44.08 |
| 14 | 1.8% H2SO4 | nmp | 140 | 20 | 6.24 | 4.88 | 65.00 | 23.88 | 68.33 |

TABLE 1-continued

Conversion of Fructose to HMF at lower temperatures in shorter time periods using microwave irradiation graphically illustrated in FIG. 1.

| Experiment # | Acid (%) | Solvent | Temp (C.) | Time (min) | Water (%) | Fructose Yield (%) | HMF Yield (%) | Unknown Yield (%) | Conversion (%) |
|---|---|---|---|---|---|---|---|---|---|
| 15 | none | water | 200 | 3 | 89.68 | 15.96 | 56.10 | 27.94 | 66.75 |
| 16 | none | water | 210 | 3.5 | 90.94 | 7.56 | 51.12 | 41.32 | 55.30 |
| 17 | none | water | 220 | 3.5 | 92.67 | 5.94 | 26.26 | 67.81 | 27.91 |
| 18 | none | water | 190 | 3 | 84.18 | 59.01 | 22.57 | 18.43 | 55.05 |

The data from this table summarizing relative conversion of fructose and production of HMF is HMF ethers can also be made directly under similar reaction conditions if fructose is used as the starting material and reaction solvent is an alcohol. Any organic alcohol or alcohol mixture can be used, including allyl, alkyl, aryl, and cycloalkyl alcohols. In most practical embodiments a C1 to C8 alcohol would be used, such as methanol, ethanol, propanols, primary and branched alcohols, and amyl or isoamyl alcohol.

Exemplary HMF ethers, include, but are not limited to, ethoxymethylfurfural, butoxymethylfurfural, isoamyloxyfurfural, and methoxymethylfurfural inter alia or any combination thereof. In addition, the reaction product may comprise corresponding HMF esters, exemplified, 5-acetoxymethylfurfural, inter alia and any combination thereof.

The reaction mixture preferably contains a catalyst and exemplary catalyst include the same heterogeneous and homogeneous acid catalyst in the same amounts mentioned for HMF synthesis. Typical reaction conditions include irradiating the mixture containing fructose, the catalyst and the alcohol solvent to bring it a temperature of between 140 to about 200° C. for a time sufficient to convert at least 50% of the fructose to the HMF ether derivative of the alcohol solvent. Typical reaction times are only 30 minutes or less. Temperatures toward the higher end of the range will lead to production of more HMF ether, but also more levulinic acid ester derivatives than lower temperatures. Thus, for example, when the reaction was conducted at 160° C. for 10 minutes in the presence of isoamyl alcohol and $H_2SO_4$ catalyst, about 16% of the reaction product was to isoamyl levulinate and about 55% was the isoamyloxyfurfural derivative. At 200° C. for 30 minutes under the same conditions, about 18% of the reaction product was to isoamyl levulinate but about 59% was the isoamyloxyfurfural derivative.

Levulinic Acid Esters:

To selectively make the levulinic acid ester derivatives, it is preferable to start with a sugar source that contains larger amounts of glucose. Formation of the levulinic acid esters also entails use of the heterogeneous or homogeneous acid catalyst and the solvent again should be, or contain, the same type of alcohols mentioned above from making HMF derivatives.

In typical embodiments, dextrose (glucose obtained by hydrolysis of starch) is combined with the alcohol and acid catalyst and heated to a temperature of between 130 and 200° C. by contact with microwave radiation for a period of 15 to 45 minutes to yield a reaction product that is at least 40% levulinate ester. In exemplary embodiments, dextrose in ethanol was combined with a heterogeneous acidic resin (Amberlyst 35) and heated to 170° C. for a period of 30 minutes after a temperature ramp-up period of 7 minutes. The product yield was typically about 50% of ethyl levulinate from dextrose. Smaller side products included HMF at about 12% and the HMF ether derivative, ethoxymethyl furfural at about 25.4%

Exemplary levulinic esters include, but are not limited to, butyl levulinate, ethyl levulinate, and isoamyl levulinate inter alia and any combination thereof. In certain embodiments, reaction yields of levulinate esters can be very high.

Extraction Steps.

In certain embodiments, after an aqueous mixture of sugar has been irradiated for a sufficient time to convert at least a portion of the sugar into HMF or derivatives including HMF esters, HMF ethers, and levulinate esters, an immiscible organic solvent may be added to the mixture, which can be filtered or unfiltered, thereby partitioning the HMF and its derivatives into an organic phase solution; the organic phase solution may be collected; and the solvent may be evaporated, e.g., under a reduced atmospheric pressure, from the organic phase solution to produce an extract enriched with HMF and its derivatives or levulnic acid derivatives. Examples of organic solvents that may be used include, but are not limited to, ethyl acetate, methyl t-butyl ether, diether ether, toluene, methyl ethyl ketone, ethyl lactate, methyl isobutyl ketone, octanol, pentanol, butyl acetate, chloroform, and any combination thereof. In addition, the aqueous phase may be collected and the unreacted fructose can be irradiated again to produce HMF and its derivatives and levulinate esters, or it can be recycled for another purpose disclosed herein or known in the art.

The disclosed extraction method is particularly advantageous, as it eliminates the need for a multi-step purification process, thereby improving speed and efficiency while reducing costs and waste. The extracted reaction products may then be used as a reactant source for further transformation into a variety of useful derivatives or recrystallized to further increase the purity of the reaction product.

Anhydrosugar alcohols can also be efficiently made using microwave radiation. To make anhydrosugar alcohols, the initial reagent is typically a sugar alcohol, particularly a hexitol, that is irradiated for a sufficient time to dehydrate the sugar alcohol into a mono- or dianhydrosugar alcohol. Examples of sugar alcohols that may be converted to anhydrosugar alcohols include, but are not limited to, monoanhydro sugar alcohol, dianhydro sugar alcohol, hexose, fructose, sorbitol, erythritol, theitol, xylitol, arabitol, ribotol, mannitol, galactitol, iditol, lactitol, isomalt, maltitol, and any combinations thereof.

The solvent can be an aqueous solvent or a polar organic solvent or combinations of the same. Preferred polar organic solvents are aprotic solvent. Examples of possible solvents include, but are not limited to, 1-methyl-2-pyrrolidinone, dimethylacetamide, dimethylformamide, dimethyl sulfoxide, methyl ethyl ketone, methyl isobutyl ketone, acetonitrile, propionitrile, and any combinations thereof. The reaction mixture typically also includes a heterogeneous or homogeneous acid a catalyst as has been described herein before for HMF production.

A mixture containing the sugar alcohol with the optional catalyst is heated with microwave irradiation for a time and at a temperature needed to promote the dehydration of sugar alcohol into an anhydrosugar alcohol. For example, in certain practices, the process is performed at a temperature range of 130° C. to 200° C. In some other embodiments, a temperature range of 170° C. to 190° C. may be employed. In certain embodiments, the process may be performed at a time range of 3 to 45 minutes. Typical embodiments employ a ramp up to temperature time in a range of 3 to 4 minutes. In typical embodiments, 30 minutes is sufficient for of greater than 50% of the hexitol into a mixture of monoanhydro and dianhydrosugar alcohols. In a typical 30 minute reaction, the predominant reaction product is a mono anhydrosugar alcohol, exemplified by sorbitan. Longer reaction times will result in further dehydration to produce greater amounts of the dianhydrosugar alcohol exemplified by isosorbide. It is anticipated that reaction times of less than 2 hours will be sufficient to convert most of the hexitol into the dianhydrosugar alcohol derivative.

Microwave assisted synthesis of isosorbide and sorbitan allows for the enhancement of reaction rates, ease of manipulation, and precise control over reaction rates. Following preparation, the anhydrosugar alcohols may be further purified. One preferred purification is accomplished by use of a film evaporator.

Anhydrosugar alcohol ethers can also be efficiently made from the anhydrosugar alcohols using microwave assisted irradiaton. Isosorbide dimethyl ether may be used for various applications including, but not limited to, industrial solvents, pharmaceutical additives, and personal care products.

One aspect of forming ethers from anhydrosugar alcohols is the use of dialkyl carbonates at greatly reduced temperatures pressures, and times. In prior reactions, use of dialkyl carbonates to form the corresponding alkyl ether derivatives of isosorbide required temperatures of 240-260° C., pressures of 4 MPa, and reaction times of two hours or greater. In the present teaching, the reaction can be done by irradiating the mixture with microwaves to temperatures as low as 120-170° C. in as little as 10-30 minutes. In an exemplary embodiment using isosorbide and dimethyl carbonate, the microwave power was 1000 watts, the reaction temperature was 150° C. with a ramp-up to temperature time of 2 minutes and continued microwave exposure was use to maintain that temperature for only 15 minutes. Typically the starting anhydrosugar alcohol is dissolved in a dialkyl carbonate solvent, which also serves as the alkylating reactant, however any solvent that can dissolve the reactants and products would be suitable so long as sufficient molar amounts of dialkyl carbonate are present. The alkyl group of the dialkyl carbonates can be of any length soluble in the solvent and may comprise aryl, or cycloalkyl or allyl moieties. A base catalyst is preferentially used. One exemplary base catalyst is dimethlyaminopyridine (DMAP). Other bases including non nucleophilic organic bases, sodium methoxide, solid supported bases, basic resins, weak inorganic bases, and strong inorganic bases may also be applied. This method is very beneficial as it increases the selectivity of the reaction. For example, a weak base would increase the product selectivity towards the monoalkylether. Alternatively, if a strong base is used, the dialkylether would be favored. Therefore, the choice of base would allow for more control over the product selectivity.

Another derivative compound of isosorbide that can be made by a similar process is isosorbide dinitrate. Isosorbide dinitrate may be used for various applications including, but not limited to, medication to relieve the pain of angina attacks and reduce attacks by increasing blood flow to the heart. It is made by substituting dimethyl nitrate for the dialkyl carbonate and otherwise conducting the same steps with microwave irradiation.

The various embodiments of the present disclosure may be better understood when read in conjunction with the following examples.

EXAMPLES

The following examples illustrate various non-limiting embodiments of the compositions and methods of the present disclosure and are not restrictive of the invention as otherwise described herein. Unless otherwise indicated, all percentages are by weight. The yields disclosed herein are exemplary and do not reflect the optimal yields under optimized conditions.

Example 1

Preparation of HMF in Dimethylacetamide

A mixture of crystalline fructose (10 g) in dimethylacetamide (30 mL) and Amberlyst 35 wet resin (Rohm and Haas, Woodridge, Ill.) was placed in a sealed Teflon-lined-reaction vessel inside a high-density rotor for treatment in a MicroSYNTH Microwave Labstation. The sample was heated via microwaves from room temperature to 65° C. in 1.5 min., then to 130° C. in 1 min., and kept at 130° C. for 15 min. using an irradiation power of 1000 Watts. The vessel was cooled. Analysis indicates a 42% molar yield of HMF from fructose and 69% conversion (See Experiment 5 in Table 1).

Example 2

Preparation of HMF in Dimethylformamide

A mixture of crystalline fructose (10 g) in dimethylformamide (30 mL) and Amberlyst 35 wet resin (5 g, Rohm and Haas, Woodridge, Ill.) was placed in a sealed Teflon-lined reaction vessel inside a high-density rotor for treatment in a MicroSYNTH Microwave Labstation. The sample was heated via microwaves from room temperature to 65° C. in 1.5 min., then to 130° C. in 1 min., and kept at 130° C. for 15 min. using an irradiation power of 1000 Watts. The vessel was cooled. Analysis indicates a 41% molar yield of HMF from fructose and 71% conversion (See Experiment 3 in Table 1).

Example 3

Preparation of HMF in NMP

In a first experiment, a mixture of crystalline fructose (10 g) in NMP (25 mL) and concentrated $H_2SO_4$ (0.1 mL) was placed in a sealed Teflon-lined reaction vessel inside a high-density rotor for treatment in a MicroSYNTH Microwave Labstation. The sample was heated via microwaves from room temperature to 140° C. in 3 min., and kept there for 20 min. using an irradiation power of 1000 Watts. The vessel was cooled. Analysis indicates a 65% molar yield of HMF from fructose.

In another experiment, a mixture of crystalline fructose (10 g) in NMP (25 mL) and concentrated $H_2SO_4$ (0.1 mL) was placed in a sealed Teflon-lined reaction vessel inside a high-density rotor for treatment in a MicroSYNTH Microwave Labstation. The sample was heated from room temperature to 160° C. in 3 min., and kept there for 20 min. using an irradiation power of 1000 Watts. The vessel was cooled. Analysis indicates a 77% molar yield of HMF from fructose. These same conditions, when performed with a conventional heating system, produced 65% molar yield of HMF.

In the third experiment, a mixture of crystalline fructose (10 g) in NMP (25 mL) and concentrated $H_2SO_4$ (0.05 mL) was placed in a sealed Teflon-lined reaction vessel inside a high-density rotor for treatment in a MicroSYNTH Microwave Labstation. The sample was heated from room temperature via microwaves to 160° C. in 3 min. and kept there for 20 min. using an irradiation power of 1000 Watts. The vessel was cooled. Analysis indicates a 70% molar yield of HMF from fructose (See Experiment 14 in Table 1). These same conditions, when performed with a conventional heating system, produced 54% molar yield of HMF.

Example 4

Preparation of HMF in Water

In a first experiment, a mixture of crystalline fructose (10 g) in water (25 mL) and concentrated $H_2SO_4$ (0.1 mL) was placed in a sealed Teflon-lined reaction vessel inside a high-density rotor for treatment in a MicroSYNTH Microwave Labstation. The sample was heated via microwaves from room temperature to 140° C. in 3 min., and kept there for 10 min. using an irradiation power of 1000 Watts. The vessel was cooled. Analysis indicates a 20% molar yield of HMF from fructose and 44% conversion Example 5

Preparation of HMF in Water

In a first experiment, a mixture of crystalline fructose (10 g) in water (40 mL) was placed in a sealed Teflon-lined reaction vessel inside a high-density rotor for treatment in a MicroSYNTH Microwave Labstation. The sample was heated from room temperature via microwaves to 200° C. in 3 min., and kept there for 3 min. using an irradiation power of 1000 Watts. The vessel vas cooled. Analysis indicates a 54% molar yield of HMF from fructose and 63% conversion. These same conditions, when performed with a conventional heating system, produced 1% molar yield of HMF.

In a second experiment, a mixture of crystalline fructose (10 g) in water (40 mL) was placed in a sealed Teflon-lined reaction vessel inside a high-density rotor for treatment in as MicroSYNTH Microwave Labstation. The sample was heated from room temperature to 210° C. in 3.5 min., and kept there for 3.5 min. using an irradiation power of 1000 Watts. The vessel was cooled. Analysis indicates a 52% molar yield HMF from fructose and 55% conversion.

Example 6

Preparation of Isoamyl HMF

In a first experiment, a mixture of crystalline fructose (10 g) in isoamyl alcohol (40 mL) and concentrated $H_2SO_4$ (0.10 mL) was placed in sealed a Teflon-lined reaction vessel inside a high-density rotor for treatment in a MicroSYNTH Microwave Labstation. The sample was heated from room temperature via microwaves to 200° C. in 3 min., and kept there for 3 min. using an irradiation power of 1000 Watts. The vessel was cooled. Analysis indicates a 59% molar yield of isoamyl HMF and 18% yield of isoamyl levulinate from fructose.

In the second experiment, a mixture of crystalline fructose (10 g) in isoamyl alcohol (40 mL) and concentrated $H_2SO_4$ (0.10 mL) was placed in a sealed Teflon-lined reaction vessel inside a high-density rotor for treatment in a MicroSYNTH Microwave Labstation. The sample was heated from room temperature via microwaves to 160° C. in 3 min., and kept there for 20 min. using an irradiation power of 1000 Watts. The vessel was cooled. Analysis indicates a 61% molar yield of isoamyl HMF and 27% yield of isoamyl levulinate from fructose. These same conditions, when performed with a conventional heating system, produced 33% molar yield of isoamyl HMF and 24% molar yield of isoamyl levulinate.

In the third experiment, a mixture of crystalline fructose (10 g) in isoamyl alcohol (40 mL) and concentrated $H_2SO_4$ (0.10 mL) was placed in a sealed Teflon-lined reaction vessel inside a high-density rotor for treatment via microwaves in a MicroSYNTH Microwave Labstation. The sample was heated from room temperature to 160° C. in 3.5 min., and kept there for 10 min. using an irradiation power of 1000 Watts. The vessel was cooled. Analysis indicates a 55% molar yield of isoamyl HMF and 16% yield of isoamyl levulinate from fructose.

Example 7

Purification of HMF From A Reaction Mixture

The material prepared as described in Example 5 was filtered by gravity filtration. Ethyl acetate (120 mL) was added to the solution, and two layers separated. The organic layer was dried over $M_gSO_4$, and the solvent evaporated to provide 3.36 g of bright red oil which was 64.4% HMF.

Example 8

Preparation of Levulinate Ester

In a first experiment, a mixture of crystalline dextrose (4 g) in ethanol (40 mL) and dry Amberlyst 35 resin (4 g) was placed in a sealed Teflon-lined reaction vessel inside a high-density rotor for treatment via microwaves in a MicroSYNTH Microwave Labstation. The sample was heated from room temperature to 170° C. in 7 min. and maintained at this temperature for 30 min. using an irradiation power of 1000 Watts. The vessel was then cooled. Analysis indicated a 49.4% molar yield of ethyl levulinate 12.3% molar yield of HMF and 3% molar yield of ethoxymethylfurfural from dextrose. These same conditions, when performed using conventional heating methods, provided 24% molar yield of ethyl levulinate, 9% dextrose, and 2% yield of HMF.

In a second experiment, a mixture of crystalline dextrose (7 g) in ethanol (70 mL) and dry Amberlyst 35 resin (7.02 g) was placed in a sealed Teflon-lined reaction vessel inside a high-density rotor for treatment via microwaves in a MicroSYNTH Microwave Labstation. The sample was heated from room temperature to 170° C. in 7 min and maintained at this temperature for 30 min. using an irradiation power of 1000 Watts. The vessel was then cooled. Analysis indicated a 49.3% molar yield of ethyl levulinate from dextrose.

In a third experiment, a mixture of crystalline dextrose (7 g) in ethanol (70 mL) and dry Amberlyst 35 resin (3.54 g) was place in a sealed Teflon-lined reaction vessel inside a high density rotor for treatment via microwaves in a MicroSYNTH Microwave Labstation. The sample was heated from room temperature to 170° C. in 7 min., and kept there for 30 min.

using an irradiation power of 1000 Watts. The vessel was then cooled. Analysis indicated a 25.4% molar yield of ethyl levulinate from dextrose.

Example 9

Preparation of Furfural

In an experiment, a mixture of crystalline xylose (10 g) in ethanol (50 mL) and sulfuric acid (2% by wt of sugar) was placed in a sealed Teflon-lined vessel inside a high-density rotor for treatment via microwaves in a MicroSYNTH Microwave Labstation. The sample was heated from room temperature to 170° C. in 4 min. and maintained at this temperature for 20 min. using an irradiation power of 1000 Watts. The vessel was then cooled. Analysis indicated a 27% molar yield of furfural from xylose.

Example 10

Preparation of Isosorbide From Sorbitol Using Microwave Irradiation at 170° C. and Sulfuric Acid A 70% sorbitol solution (50 g) and concentrated sulfuric acid (0.20 mL) was placed in a TEFLON®-lined reaction vessel inside a high density rotor for treatment in a MICROSYNTH® Microwave Labstation. The sample was heated from room temperature to 170° C. in 3 minutes, and kept at 170° C. for 30 minutes using microwave irradiation at a power of 1000 watts. The reaction mixture was then cooled. The final product was composed of 50.4% sorbitan, 7.8% isosorbide, and 11.9% sorbitol.

Example 11

Preparation of Isosorbide From Sorbitol Using Microwave Irradiation at 190° C. and Sulfuric Acid A 70% sorbitol solution (50 g) and concentrated sulfuric acid (0.20 mL) was placed in a TEFLON®-lined reaction vessel inside a high density rotor for treatment in a MicroSYNTH® Microwave Labstation. The sample was heated from room temperature to 190° C. in 4 minutes, and kept at 190° C. for 30 min using a microwave irradiation at a power of 1000 watts. The vessel was cooled. The final product was composed of 39.6% sorbitan, 16.5% isosorbide, and 0.8% sorbitol.

Example 12

Preparation of Isosorbide From Sorbitol Using Microwave Irradiation at 190° C. and Sulfuric Acid A 70% sorbitol solution (50 g) and concentrated sulfuric acid (0.10 mL) was placed in a TEFLON®-lined reaction vessel inside a high density rotor for treatment in a MicroSYNTH® Microwave Labstation. The sample was heated from room temperature to 190° C. in 4 minutes, and kept at 190° C. for 30 minutes using a microwave irradiation at a power of 1000 watts. The vessel was cooled. The final product was composed of 43.4% sorbitan, 9.5% isosorbide, and 6.0% sorbitol.

Example 13

Preparation of Dimethyl Isosorbide From Isosorbide

Isosorbide (3 g), dimethylaminopyridine (0.16 g), and dimethyl carbonate (30 mL) was placed in a Teflon-lined reaction vessel inside a high density rotor for treatment in a MicroSYNTH Microwave Labstation. The sample was heated from room temperature to 150° C. in 2 min, and kept at 150° C. for 15 min using an irradiation power of 1000 Watt. The vessel was cooled. TLC analysis indicates a decrease in the amount of isosorbide and a significant amount of dimethyl isosorbide. Monomethyl isosorbide may also be present. The use of MW with dimethyl carbonate as a means of alkylating anhydrosugar alcohols is novel.

What is claimed is:

1. A method of producing a dehydrated sugar derivative comprising,
   a. forming a reaction mixture comprising a solvent and a reactant selected from the group consisting of a hexose, a sugar alcohol, and an anhydrosugar alcohol, and an acidic catalyst selected from the group consisting of a heterogeneous solid acid substrate and a homogeneous acid; and
   b. contacting the reaction mixture with microwave radiation to achieve a temperature of between 160° C. and 210° C. for a time sufficient to convert at least 40% of the reactant into at least one desired dehydrated sugar derivative product,
      wherein the reaction contains a R-alcohol selected from the group consisting of an alkyl group, an allyl group, a cycloalkyl group, an aryl group, and combinations of any thereof; wherein
      the reactant is present in a concentration of at least 20%; and
      the R-alcohol is the solvent in the reaction mixture; and,
      the dehydrated sugar derivative is selected from the group consisting of an R-ether or R-ester of the dehydrated sugar.

2. The method of claim 1 wherein the reactant is a hexose and the desired dehydrated sugar derivative is selected from the group consisting of a hydroxymethylfurfural ether and a levulinate ester; in particular when the hexose is glucose, the levulinate ester is the predominant desired dehydrated sugar derivative and when the hexose is fructose, the predominant desired dehydrated sugar derivative is the hydroxymethylfurfural ether.

3. The method of claim 2 wherein the acid catalyst is a homogeneous acid and the desired dehydrated sugar derivative is the levulinate ester.

4. The method of claim 2 wherein the acid catalyst is a solid acid resin and the desired dehydrated sugar derivative is hydroxymethylfurfural ether.

5. The method of claim 1, further including at least partially purifying the desired dehydrated derivative from the reaction mixture by at least:
   adding an immiscible organic solvent to the mixture, thereby partitioning the dehydrated sugar derivative into immiscible organic solvent solution;
   collecting the partitioned immiscible organic solvent; and
   evaporating the collected solvent to produce an extract enriched in the desired dehydrated sugar derivative.

6. The method of claim 5, wherein the immiscible organic solvent is selected from the group consisting of ethyl acetate, methyl t-butyl ether, diethyl ether, toluene, methyl ethyl ketone, ethyl lactate, methyl isobutyl ketone, octanol, pentanol, butyl acetate, chloroform, and any combinations thereof.

* * * * *